United States Patent
Baril et al.

(10) Patent No.: US 11,172,915 B2
(45) Date of Patent: Nov. 16, 2021

(54) SPECIMEN RETRIEVAL DEVICES WITH SELECTIVE BAG RELEASE

(71) Applicant: COVIDIEN LP, Mansfield, MA (US)

(72) Inventors: Jacob C. Baril, Norwalk, CT (US); Saumya Banerjee, Hamden, CT (US); George S. Matta, Plainville, MA (US); Matthew A. Dinino, Newington, CT (US); Justin J. Thomas, New Haven, CT (US); Roy J. Pilletere, North Haven, CT (US)

(73) Assignee: Covidien LP, Mansfield, MA (US)

( * ) Notice: Subject to any disclaimer, the term of this patent is extended or adjusted under 35 U.S.C. 154(b) by 293 days.

(21) Appl. No.: 16/392,783

(22) Filed: Apr. 24, 2019

(65) Prior Publication Data
US 2020/0337686 A1    Oct. 29, 2020

(51) Int. Cl.
*A61B 17/00*   (2006.01)
*A61B 34/35*   (2016.01)

(52) U.S. Cl.
CPC ........ *A61B 17/00234* (2013.01); *A61B 34/35* (2016.02); *A61B 2017/00287* (2013.01); *A61B 2017/00867* (2013.01)

(58) Field of Classification Search
CPC .... A61B 2017/00287; A61B 17/00234; A61B 17/221; A61B 17/2212; A61B 2017/2215; A61B 2017/2217; A61B 2017/00867
See application file for complete search history.

(56) References Cited

U.S. PATENT DOCUMENTS

| | | | |
|---|---|---|---|
| 30,471 | A | 10/1860 | Dudley |
| 35,164 | A | 5/1862 | Logan et al. |
| 156,477 | A | 11/1874 | Bradford |
| 1,609,014 | A | 11/1926 | Dowd |
| 3,800,781 | A | 4/1974 | Zalucki |
| 4,557,255 | A | 12/1985 | Goodman |
| 4,611,594 | A | 9/1986 | Grayhack et al. |
| 4,744,363 | A | 5/1988 | Hasson |
| 4,790,812 | A | 12/1988 | Hawkins, Jr. et al. |
| 4,852,586 | A | 8/1989 | Haines |
| 4,927,427 | A | 5/1990 | Kriauciunas et al. |

(Continued)

FOREIGN PATENT DOCUMENTS

| | | |
|---|---|---|
| DE | 3542667 A1 | 6/1986 |
| DE | 3435489 U1 | 8/1986 |

(Continued)

OTHER PUBLICATIONS

European Search Report EP 12191639.9 dated Feb. 20, 2013.
(Continued)

*Primary Examiner* — Katherine H Schwiker
(74) *Attorney, Agent, or Firm* — Carter, DeLuca & Farrell LLP

(57) ABSTRACT

A specimen retrieval device includes an elongated shaft assembly having a proximal end portion and a distal end portion. An end effector is supported on the distal end portion of the elongated shaft assembly and includes a first arm and a second arm. The first arm includes a first distal finger and the second arm includes a second distal finger. The first and second fingers are configured to selectively engage one another to support a collection bag on the first and second arms.

7 Claims, 5 Drawing Sheets

(56) References Cited

U.S. PATENT DOCUMENTS

| | | |
|---|---|---|
| 4,977,903 A | 12/1990 | Haines |
| 4,991,593 A | 2/1991 | LeVahn |
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,224,930 A | 7/1993 | Spaeth et al. |
| 5,234,439 A | 8/1993 | Wilk et al. |
| 5,279,539 A | 1/1994 | Bohan et al. |
| 5,312,416 A | 5/1994 | Spaeth et al. |
| 5,320,627 A | 6/1994 | Sorensen et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,443,472 A | 8/1995 | Li |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,611,803 A | 3/1997 | Heaven et al. |
| 5,618,296 A | 4/1997 | Sorensen et al. |
| 5,630,822 A | 5/1997 | Hermann et al. |
| 5,642,282 A | 6/1997 | Sonehara |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,681,324 A | 10/1997 | Kammerer et al. |
| 5,720,754 A | 2/1998 | Middleman et al. |
| 5,735,289 A | 4/1998 | Pfeffer et al. |
| 5,741,271 A | 4/1998 | Nakao et al. |
| 5,755,724 A | 5/1998 | Yoon |
| 5,759,187 A | 6/1998 | Nakao et al. |
| 5,769,794 A | 6/1998 | Conlan et al. |
| 5,782,840 A | 7/1998 | Nakao |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,829,440 A | 11/1998 | Broad, Jr. |
| 5,836,953 A | 11/1998 | Yoon |
| 5,853,374 A | 12/1998 | Hart et al. |
| 5,895,392 A | 4/1999 | Riek et al. |
| 5,904,690 A | 5/1999 | Middleman et al. |
| 5,906,621 A | 5/1999 | Secrest et al. |
| 5,908,429 A | 6/1999 | Yoon |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,007,546 A | 12/1999 | Snow et al. |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternstrom |
| 6,156,055 A | 12/2000 | Ravenscroft |
| 6,162,235 A | 12/2000 | Vaitekunas |
| 6,165,121 A | 12/2000 | Alferness |
| 6,168,603 B1 | 1/2001 | Leslie et al. |
| 6,206,889 B1 | 3/2001 | Bennardo |
| 6,228,095 B1 | 5/2001 | Dennis |
| 6,258,102 B1 | 7/2001 | Pagedas |
| 6,264,663 B1 | 7/2001 | Cano |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,368,328 B1 | 4/2002 | Chu et al. |
| 6,383,195 B1 | 5/2002 | Richard |
| 6,383,196 B1 | 5/2002 | Leslie et al. |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,547,310 B2 | 4/2003 | Myers |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,958,069 B2 | 10/2005 | Shipp et al. |
| 6,971,988 B2 | 12/2005 | Orban, III |
| 6,994,696 B2 | 2/2006 | Suga |
| 7,014,648 B2 | 3/2006 | Ambrisco et al. |
| 7,018,373 B2 | 3/2006 | Suzuki |
| 7,052,454 B2 | 5/2006 | Taylor |
| 7,052,501 B2 | 5/2006 | McGuckin, Jr. |
| 7,090,637 B2 | 8/2006 | Danitz et al. |
| 7,115,125 B2 | 10/2006 | Nakao et al. |
| 7,270,663 B2 | 9/2007 | Nakao |
| 7,273,488 B2 | 9/2007 | Nakamura et al. |
| 7,410,491 B2 | 8/2008 | Hopkins et al. |
| 7,547,310 B2 | 6/2009 | Whitfield |
| 7,618,437 B2 | 11/2009 | Nakao |
| 7,670,346 B2 | 3/2010 | Whitfield |
| 7,722,626 B2 | 5/2010 | Middleman et al. |
| 7,762,959 B2 | 7/2010 | Bilsbury |
| 7,785,251 B2 | 8/2010 | Wilk |
| 7,819,121 B2 | 10/2010 | Amer |
| 7,837,612 B2 | 11/2010 | Gill et al. |
| RE42,050 E | 1/2011 | Richard |
| 7,892,242 B2 | 2/2011 | Goldstein |
| 8,016,771 B2 | 9/2011 | Orban, III |
| 8,057,485 B2 | 11/2011 | Hollis et al. |
| 8,075,567 B2 | 12/2011 | Taylor et al. |
| 8,097,001 B2 | 1/2012 | Nakao |
| 8,152,820 B2 | 4/2012 | Mohamed et al. |
| 8,172,772 B2 | 5/2012 | Zwolinski et al. |
| 8,206,401 B2 | 6/2012 | Nakao |
| 8,337,510 B2 | 12/2012 | Rieber et al. |
| 8,343,031 B2 | 1/2013 | Gertner |
| 8,348,827 B2 | 1/2013 | Zwolinski |
| 8,388,630 B2 | 3/2013 | Teague et al. |
| 8,409,112 B2 | 4/2013 | Wynne et al. |
| 8,409,216 B2 | 4/2013 | Parihar et al. |
| 8,409,217 B2 | 4/2013 | Parihar et al. |
| 8,414,596 B2 | 4/2013 | Parihar et al. |

(56) References Cited

U.S. PATENT DOCUMENTS

| | | | |
|---|---|---|---|
| 8,419,749 B2 | 4/2013 | Shelton, IV et al. | |
| 8,425,533 B2 | 4/2013 | Parihar et al. | |
| 8,430,826 B2 | 4/2013 | Uznanski et al. | |
| 8,435,237 B2 | 5/2013 | Bahney | |
| 8,444,655 B2 | 5/2013 | Parihar et al. | |
| 8,579,914 B2 | 11/2013 | Menn et al. | |
| 8,585,712 B2 | 11/2013 | O'Prey et al. | |
| 8,591,521 B2 | 11/2013 | Cherry et al. | |
| 8,652,147 B2 | 2/2014 | Hart | |
| 8,696,683 B2 | 4/2014 | LeVert | |
| 8,721,658 B2 | 5/2014 | Kahle et al. | |
| 8,734,464 B2 | 5/2014 | Grover et al. | |
| 8,777,961 B2 | 7/2014 | Cabrera et al. | |
| 8,795,291 B2 | 8/2014 | Davis et al. | |
| 8,821,377 B2 | 9/2014 | Collins | |
| 8,827,968 B2 | 9/2014 | Taylor et al. | |
| 8,828,023 B2 | 9/2014 | Neff et al. | |
| 8,870,894 B2 | 10/2014 | Taylor et al. | |
| 8,906,035 B2 | 12/2014 | Zwolinski et al. | |
| 8,906,036 B2 | 12/2014 | Farascioni | |
| 8,956,370 B2 | 2/2015 | Taylor et al. | |
| 8,968,329 B2 | 3/2015 | Cabrera | |
| 2002/0068943 A1 | 6/2002 | Chu et al. | |
| 2002/0082516 A1 | 6/2002 | Stefanchik | |
| 2003/0073970 A1 | 4/2003 | Suga | |
| 2003/0100909 A1 | 5/2003 | Suzuki | |
| 2003/0100919 A1 | 5/2003 | Hopkins et al. | |
| 2003/0199915 A1 | 10/2003 | Shimm | |
| 2003/0212433 A1* | 11/2003 | Ambrisco | A61B 90/06 606/200 |
| 2003/0216773 A1 | 11/2003 | Shimm | |
| 2004/0097960 A1 | 5/2004 | Terachi et al. | |
| 2004/0138587 A1 | 7/2004 | Lyons | |
| 2005/0085808 A1 | 4/2005 | Nakao | |
| 2005/0165411 A1 | 7/2005 | Orban | |
| 2005/0267492 A1 | 12/2005 | Poncet et al. | |
| 2006/0030750 A1 | 2/2006 | Amer | |
| 2006/0052799 A1 | 3/2006 | Middleman et al. | |
| 2006/0058776 A1 | 3/2006 | Bilsbury | |
| 2006/0169287 A1 | 8/2006 | Harrison et al. | |
| 2006/0200169 A1 | 9/2006 | Sniffin | |
| 2006/0200170 A1 | 9/2006 | Aranyi | |
| 2006/0229639 A1 | 10/2006 | Whitfield | |
| 2006/0229640 A1 | 10/2006 | Whitfield | |
| 2007/0016224 A1 | 1/2007 | Nakao | |
| 2007/0016225 A1 | 1/2007 | Nakao | |
| 2007/0073251 A1 | 3/2007 | Zhou et al. | |
| 2007/0088370 A1 | 4/2007 | Kahle et al. | |
| 2007/0135780 A1 | 6/2007 | Pagedas | |
| 2007/0135781 A1 | 6/2007 | Hart | |
| 2007/0186935 A1 | 8/2007 | Wang et al. | |
| 2008/0188766 A1 | 8/2008 | Gertner | |
| 2008/0221587 A1 | 9/2008 | Schwartz | |
| 2008/0221588 A1 | 9/2008 | Hollis et al. | |
| 2008/0234696 A1 | 9/2008 | Taylor et al. | |
| 2008/0255597 A1 | 10/2008 | Pravong et al. | |
| 2008/0300621 A1 | 12/2008 | Hopkins et al. | |
| 2008/0312496 A1 | 12/2008 | Zwolinski | |
| 2009/0043315 A1 | 2/2009 | Moon | |
| 2009/0082779 A1 | 3/2009 | Nakao | |
| 2009/0182292 A1 | 7/2009 | Egle et al. | |
| 2009/0192510 A1 | 7/2009 | Bahney | |
| 2009/0240238 A1 | 9/2009 | Grodrian et al. | |
| 2010/0000471 A1 | 1/2010 | Hibbard | |
| 2010/0152746 A1 | 6/2010 | Ceniccola et al. | |
| 2011/0087235 A1 | 4/2011 | Taylor et al. | |
| 2011/0184311 A1 | 7/2011 | Parihar et al. | |
| 2011/0184434 A1 | 7/2011 | Parihar et al. | |
| 2011/0184435 A1 | 7/2011 | Parihar et al. | |
| 2011/0184436 A1 | 7/2011 | Shelton, IV et al. | |
| 2011/0190779 A1 | 8/2011 | Gell et al. | |
| 2011/0190781 A1 | 8/2011 | Collier et al. | |
| 2011/0190782 A1 | 8/2011 | Fleming et al. | |
| 2011/0264091 A1 | 10/2011 | Koppleman et al. | |
| 2011/0299799 A1 | 12/2011 | Towe | |
| 2012/0046667 A1 | 2/2012 | Cherry et al. | |
| 2012/0083795 A1 | 4/2012 | Fleming et al. | |
| 2012/0083796 A1 | 4/2012 | Grover et al. | |
| 2012/0203241 A1 | 8/2012 | Williamson, IV | |
| 2013/0023895 A1 | 1/2013 | Saleh | |
| 2013/0103042 A1 | 4/2013 | Davis | |
| 2013/0116592 A1 | 5/2013 | Whitfield | |
| 2013/0184536 A1 | 7/2013 | Shibley et al. | |
| 2013/0190773 A1 | 7/2013 | Carlson | |
| 2013/0218170 A1 | 8/2013 | Uznanski et al. | |
| 2013/0245636 A1 | 9/2013 | Jansen | |
| 2013/0274758 A1 | 10/2013 | Young et al. | |
| 2013/0325025 A1 | 12/2013 | Hathaway et al. | |
| 2014/0046337 A1 | 2/2014 | O'Prey et al. | |
| 2014/0058403 A1 | 2/2014 | Menn et al. | |
| 2014/0180303 A1 | 6/2014 | Duncan et al. | |
| 2014/0222016 A1 | 8/2014 | Grover et al. | |
| 2014/0236110 A1 | 8/2014 | Taylor et al. | |
| 2014/0243865 A1 | 8/2014 | Swayze et al. | |
| 2014/0249541 A1 | 9/2014 | Kahle et al. | |
| 2014/0276913 A1 | 9/2014 | Tah et al. | |
| 2014/0303640 A1 | 10/2014 | Davis et al. | |
| 2014/0309656 A1 | 10/2014 | Gal et al. | |
| 2014/0330285 A1 | 11/2014 | Rosenblatt et al. | |
| 2014/0350567 A1 | 11/2014 | Schmitz et al. | |
| 2014/0371759 A1 | 12/2014 | Hartoumbekis | |
| 2014/0371760 A1 | 12/2014 | Menn | |
| 2015/0018837 A1 | 1/2015 | Sartor et al. | |
| 2015/0045808 A1 | 2/2015 | Farascioni | |
| 2015/0289864 A1* | 10/2015 | Holsten | A61B 10/04 606/114 |
| 2017/0049427 A1 | 2/2017 | Do et al. | |
| 2017/0215904 A1 | 8/2017 | Wassef et al. | |
| 2017/0224321 A1 | 8/2017 | Kessler et al. | |

FOREIGN PATENT DOCUMENTS

| | | | |
|---|---|---|---|
| DE | 4204210 A1 | 8/1992 | |
| DE | 19624826 A1 | 1/1998 | |
| EP | 0930047 A1 * | 7/1999 | A61B 17/00234 |
| EP | 0947166 A2 | 10/1999 | |
| EP | 1685802 A1 | 8/2006 | |
| EP | 1707126 A1 | 10/2006 | |
| EP | 2005900 A2 | 12/2008 | |
| EP | 2184014 A2 | 5/2010 | |
| EP | 2436313 A2 | 4/2012 | |
| EP | 2474270 A2 | 7/2012 | |
| FR | 1272412 A | 9/1961 | |
| GB | 246009 A | 1/1926 | |
| WO | 9315675 A1 | 8/1993 | |
| WO | 9509666 A1 | 4/1995 | |
| WO | 0135831 A1 | 5/2001 | |
| WO | 2004002334 A1 | 1/2004 | |
| WO | 2004112571 A2 | 12/2004 | |
| WO | 2005112783 A1 | 12/2005 | |
| WO | 2006110733 | 10/2006 | |
| WO | 2007048078 A1 | 4/2007 | |
| WO | 2007048085 A2 | 4/2007 | |
| WO | 2008114234 A2 | 9/2008 | |
| WO | 2009149146 A1 | 12/2009 | |
| WO | 2011090862 A2 | 7/2011 | |
| WO | 2014134285 A1 | 9/2014 | |
| WO | 2015134888 A1 | 9/2015 | |
| WO | 2016025132 A1 | 2/2016 | |
| WO | 2017189442 A1 | 11/2017 | |

OTHER PUBLICATIONS

European Search Report EP 11250837.9 dated Sep. 10, 2013.
European Search Report EP 11250838.7 dated Sep. 10, 2013.
European Search Report EP 13170118.7 dated Dec. 5, 2013.
European Search Report EP 12165852 dated Jun. 20, 2012.
http://www.biomaterials.org/week/bio17.cfm, definition and examples of hydrogels.
European Search Report EP 12150271 dated Jan. 14, 2013.
European Search Report EP 12193450 dated Feb. 27, 2013.
European Search Report EP 12189517.1 dated Mar. 6, 2013.
European Search Report EP 12158873 dated Jul. 19, 2012.

(56) References Cited

OTHER PUBLICATIONS

European Search Report EP 11250836 dated Sep. 12, 2013.
European Search Report dated Feb. 12, 2019 issued in EP Application No. 18208634.
International Search Report issued in Appl. No. PCT/US2018/058609 dated Feb. 22, 2019.

* cited by examiner

SPECIMEN RETRIEVAL DEVICES WITH SELECTIVE BAG RELEASE

TECHNICAL FIELD

This disclosure relates to surgical instruments, and more particularly, to specimen retrieval devices that support tissue collection bags.

BACKGROUND

Specimen retrieval devices are commonly used during surgical procedures to collect and remove tissue specimens from a patient. Typically, during a surgical procedure in which tissue is transected, e.g., a hysterectomy procedure, a specimen retrieval device including a tissue collection bag is positioned to receive the tissue specimen once the tissue is transected. In some procedures, a grasper may be used to transfer the transected tissue specimen into the bag. Alternately, the bag may be positioned in relation to the tissue specimen to allow the tissue specimen to fall into the bag.

SUMMARY

In aspects of the disclosure, a specimen retrieval device includes an elongated shaft assembly having a proximal end portion and a distal end portion. An end effector is supported on the distal end portion of the elongated shaft assembly and includes a first arm and a second arm. The first arm includes a first distal finger and the second arm includes a second distal finger. The first and second fingers are configured to selectively engage one another to support a collection bag on the first and second arms.

In embodiments, the first and second distal fingers may be secured together with a suture. The first distal finger may define an opening therethrough and the second distal finger may define an opening therethrough. The openings of the first and second distal fingers may be configured to receive the suture therethrough.

In some embodiments, the first distal finger may include a first detent that is selectively engagable with the second distal finger. The second distal finger may include a second detent that is selectively engageable with the first distal finger. One or both of the first and second detents may have a U-shaped configuration.

In embodiments, the first detent may include one or more wings.

In various embodiments, the specimen retrieval device may further include a stationary handle and a movable handle supported on the proximal end portion of the elongated shaft assembly. The movable handle may be movable relative to the stationary handle to move the end effector between a closed position and an open position.

In some embodiments, the specimen retrieval device may further include the collection bag. The first and second arms may be configured to retain the collection bag on the end effector when the end effector is in the closed position. The first and second arms may be configured to release the collection bag from the end effector when the end effector is in the open position.

According to another aspect of the disclosure, a specimen retrieval system includes a collection bag, a first arm, and a second arm. The first arm has a first distal finger supported on a distal end portion of the first arm. The second arm has a second distal finger supported on a distal end portion of the second arm. The first and second arms are selectively movable relative to one another to releasably secure the collection bag on the first and second arms. The first and second distal fingers are disposed in slidable engagement to retain the collection bag on the first and second arms.

In embodiments, each of first and second detents may include a pair of wings.

According to yet another aspect of the disclosure, a specimen retrieval device includes an outer shaft, an inner shaft, a first arm, and a second arm. The outer shaft has a stationary handle on a proximal end portion thereof. The inner shaft is supported within the outer shaft and has a movable handle on a proximal end portion thereof. The movable handle is positioned to move relative to the stationary handle. The first arm has a proximal end portion secured to the inner shaft and distal end portion having a first distal finger. The second arm has a proximal end portion secured to the inner shaft and distal end portion having a second distal finger. The first and second distal fingers are configured to move in opposite directions as the movable handle moves relative to the stationary handle.

In embodiments, the first and second distal fingers may be secured together with a suture to prevent the first and second distal fingers from moving relative to one another.

In various embodiments, the first distal finger may support a first winged detent and the second distal finger may support a second winged detent. In response axial translation of the movable handle relative to the stationary handle, the first winged detent may be configured to radially cam along the second distal finger and the second winged detent may be configured radially cam along the first distal finger.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 2 is an enlarged, perspective view of the indicated area of detail shown in

FIG. 1;

FIG. 10 is an enlarged, perspective view of the indicated area of detail shown in

FIG. 8;

DETAILED DESCRIPTION

Figure 1:
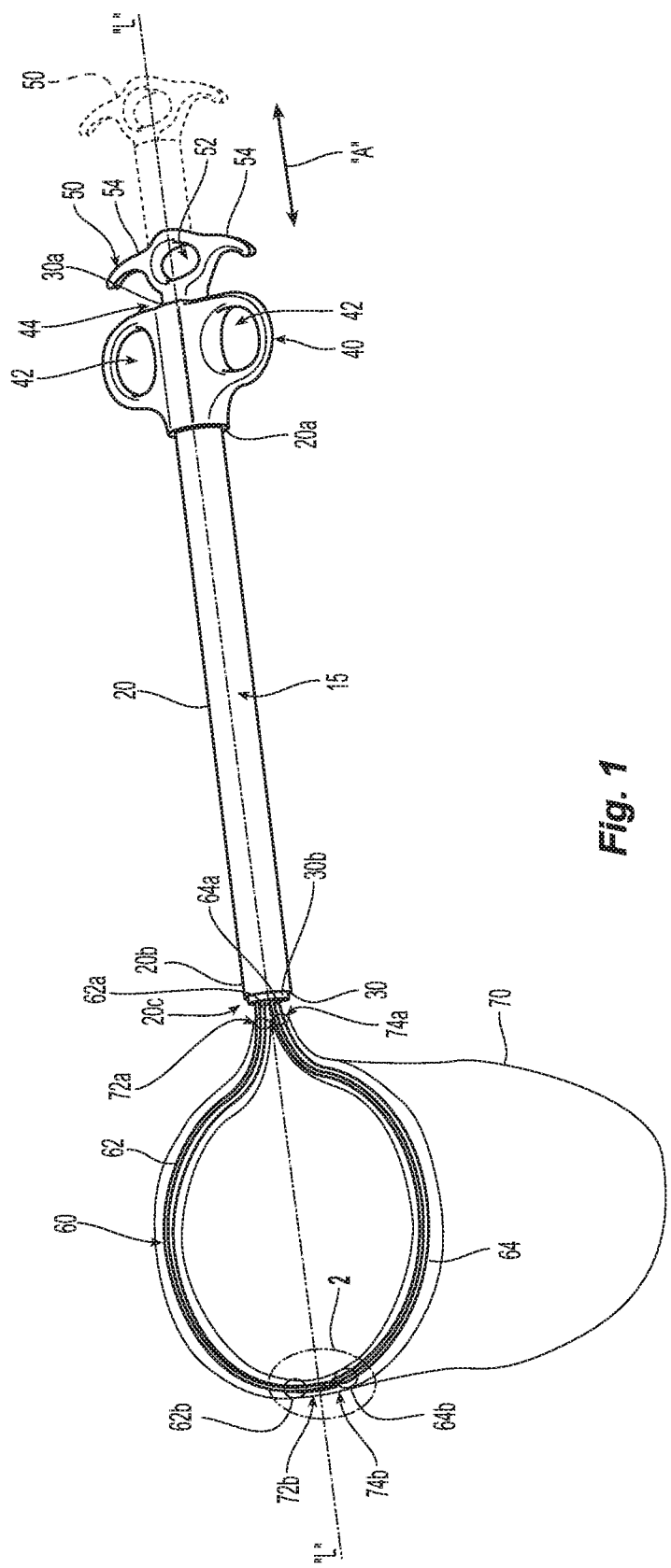
FIG. 1 is a perspective view of one embodiment of a specimen retrieval device in accordance with the principles of this disclosure, the specimen retrieval device illustrated in a closed position.

Embodiments of the disclosed specimen retrieval devices are described in detail with reference to the drawings, in which like reference numerals designate identical or corresponding elements in each of the several views. As commonly known, the term "clinician" refers to a doctor (e.g., a surgeon), a nurse, or any other care provider and may include support personnel. Additionally, the term "proximal" refers to the portion of structure that is closer to the clinician and the term "distal" refers to the portion of structure that is farther from the clinician. In the following description, well-known functions or constructions are not described in detail to avoid obscuring this disclosure in unnecessary detail.

In general, this disclosure describes a specimen retrieval device with bag release mechanisms to facilitate quick and easy removal of collection bags supported on the specimen retrieval device. In embodiments of this disclosure, a specimen retrieval device includes overlapping arms that are secured together by a suture to create a single rigid ring for supporting a collection bag and for providing leverage when loading a specimen in the collection bag. The suture may be cut to enable the arms to separate so that the collection bag can be removed from the specimen retrieval device, for instance, once a specimen is contained within the collection bag. In some embodiments of this disclosure, a specimen retrieval device includes arms having U-shaped detents that overlap to secure a collection bag to the arms. The U-shaped detents provide increased rigidity to the arms when the arms are overlapped for supporting the collection bag on the arms. The arms may be slidably releasable to enable bag release.

Figure 2:
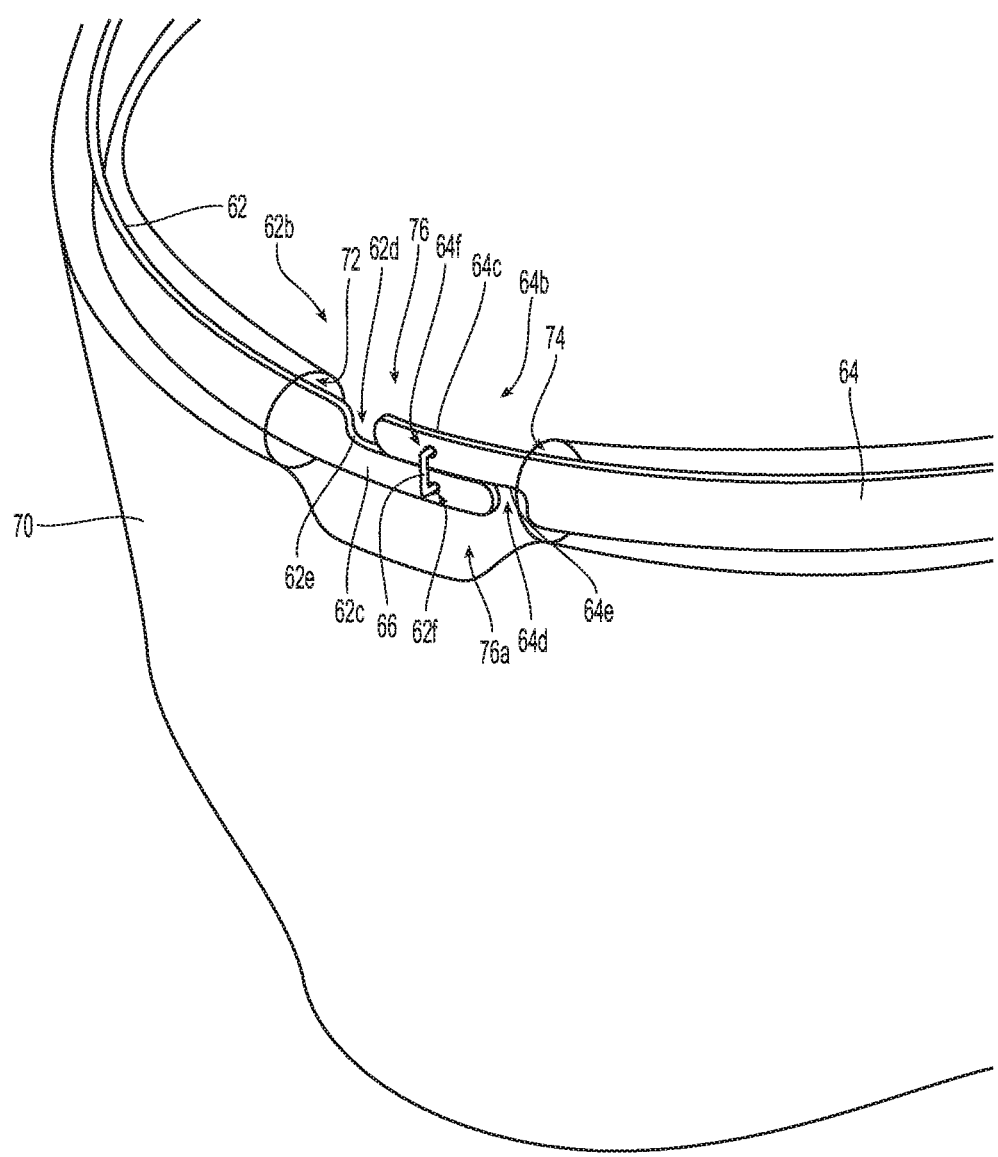
Figure 3:
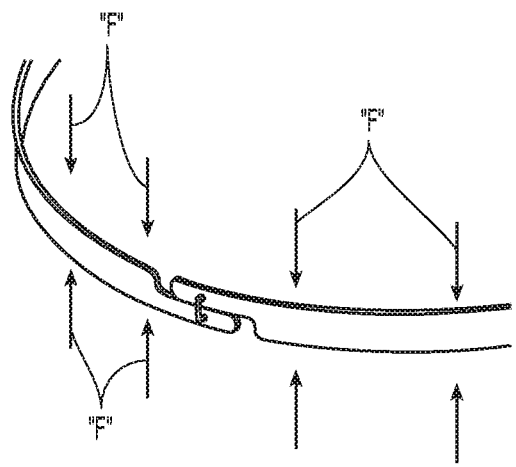
FIG. 3 is a perspective view of a distal portion of arms of the specimen retrieval device, the arms shown coupled together by a suture.

With reference to FIGS. 1-3, a specimen retrieval device 10 defines a longitudinal axis "L" and includes an elongated shaft assembly 15 having an outer shaft 20 and an inner shaft 30 supported within outer shaft 20. Outer shaft 20 has a proximal end portion 20a that supports a stationary handle 40 and a distal end portion 20b that defines a distal opening 20c. Stationary handle 40 defines finger openings 42 therethrough to facilitate grasping of stationary handle 40 by a user's fingers. Stationary handle 40 further defines a central opening 44 axially therethrough that is configured to slidably receive inner shaft 30 therein. Inner shaft 30 has a proximal end portion 30a that supports a movable handle 50 and a distal end portion 30b that supports an end effector 60. Movable handle 50 defines a finger opening 52 therethrough and includes wings 54 that extend from opposite sides of movable handle 50. Finger opening 52 and wings 54 are configured to receive a user's fingers to facilitate finger gripping. Movable handle 50 is positioned to move axially along longitudinal axis "L," and relative to stationary handle 40, between distal and proximal positions, as indicated by arrows "A."

End effector 60 of specimen retrieval device 10 supports a collection bag 70 and includes a first arm 62 and a second arm 64 that define a ring when coupled together. First arm 62, which may have a hook or question mark shape, includes a proximal end portion 62a that curves distally to a distal end portion 62b. Distal end portion 62b of first arm 62 includes a first distal finger 62c and defines a first finger recess 62d along a side surface 62e of first distal finger 62c. First distal finger 62c defines an opening 62f configured to receive suture 66 therethrough. Second arm 64, which may also have a hook or question mark shape, includes a proximal end portion 64a that curves distally to a distal end portion 64b. Distal end portion 64b of second arm 64 includes a second distal finger 64c and defines a second finger recess 64d along a side surface 64e of second distal finger 64c. Second distal finger 64c defines an opening 64f configured to receive suture 66 therethrough. First and second arms 62, 64 curve in opposite directions so as to be mirrored relative to one another about longitudinal axis "L." First and second distal fingers 62c, 64c are configured to be disposed in an overlapped arrangement (e.g., so that fingers 62c 64c, and/or openings 62f, 64f thereof are in vertical registration with one another) as seen in FIG. 2. Side surfaces 62e, 64e of first and second distal fingers 62c, 64c, respectively, are configured to cam along one another such that first and second distal fingers 62c, 64c are selectively receivable into and/or out of first and second finger recesses 62d, 64d of respective first and second arms 62, 64. Suture 66 can be looped through openings 62f, 64f of respective first and second distal fingers 62c, 64c, and tied off, to rigidly secure first and second distal fingers 62c, 64c together so that first and second arms 62, 64 form a unitary or single rigid ring that provides increased leverage against applied force when loading a specimen into collection bag 70, as indicated by arrows "F" seen in FIG. 3.

As seen in FIGS. 1 and 2, collection bag 70 includes a first arm channel 72 that has open proximal and distal ends 72a, 72b and second arm channel 74 with open proximal and distal ends 74a, 74b. First arm channel 72 slidably receives first arm 62 of end effector 60 and a second arm channel 74 slidably receives second arm 64 of end effector 60. First and second arm channels 72, 74 are separated by gap 76 that enables first and second distal fingers 62c, 64c to extend out of respective first and second arm channels 72, 74. Gap 76 provides access to openings 62f, 64f of respective first and second distal fingers 62c, 64c (e.g., to loop suture 66 therethrough for connecting first and second distal fingers 62c, 64c together) and/or access to suture 66 (e.g., for removing suture 66 to disconnect first and second distal fingers 62c, 64c). Gap 76 may include a recess 76a that extends below first and second arm channels 72, 74 to increase accessibility to first and second distal fingers 62c, 64c and/or suture 66, and which may provide increased visualization, for instance, while end effector 60 is disposed in a patient's body.

Figure 4:
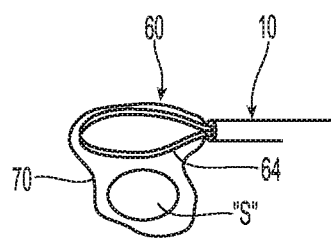
FIGS. 4-7 are progressive views illustrating the specimen retrieval device receiving a specimen in a collection bag of the specimen retrieval device, and moving the arms from the closed position to an open position to release the collection bag from the specimen retrieval device with the specimen contained within the collection bag.
Figure 5:
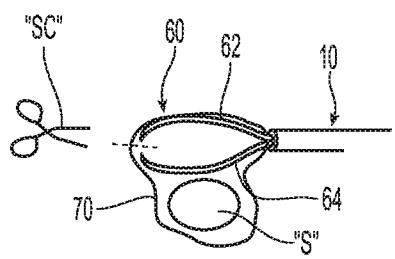
Figure 6:
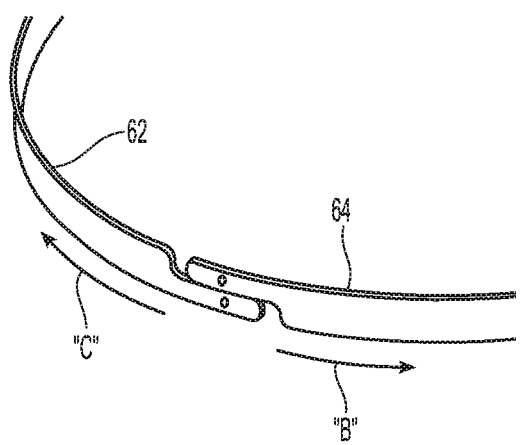
Figure 7:
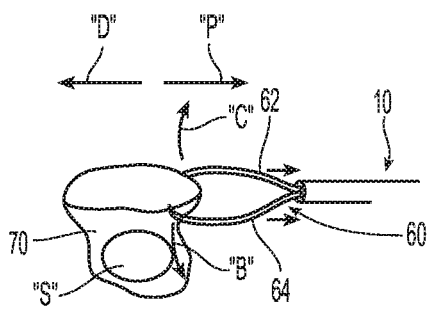

As illustrated in FIGS. 1-7, specimen retrieval device 10 can be provided in a retrieval configuration in which collection bag 70 is mounted to first and second arms 62, 64 of end effector 60, suture 66 is tied to first and second distal fingers 62c, 64c of respective first and second arms 62, 64, and movable handle 50 is disposed in a distal position in which movable handle 50 may be in contact with, or at least in close approximation to stationary handle 40 so that specimen retrieval device 10 can be positioned for collecting a specimen. Once a specimen "S" is collected in collection bag 70 of specimen retrieval device 10, as seen in FIG. 4, suture 66 can be removed, such as by untying or cutting with a sharpened instrument like scissors "SC," as seen in FIG. 5. With suture 66 removed from first and second arms 62, 64, movable handle 50 can be retracted proximally to cause first and second arms 62, 64 to move in radially opposite directions relative to one another, as indicated by arrows "B"

and "C," to separate first and second arms 62, 64. Once first and second arms 62, 64 are separated, collection bag 70 can be slid (e.g., in a distal direction "D") off distal end portions 62b, 64b of first and second arms 62, 64 and/or end effector 60 can be retracted proximally relative to collection bag 70 (e.g., in a proximal direction "P") to facilitate removal of collection bag 70 from end effector 60, as seen in FIG. 7.

Figure 8:
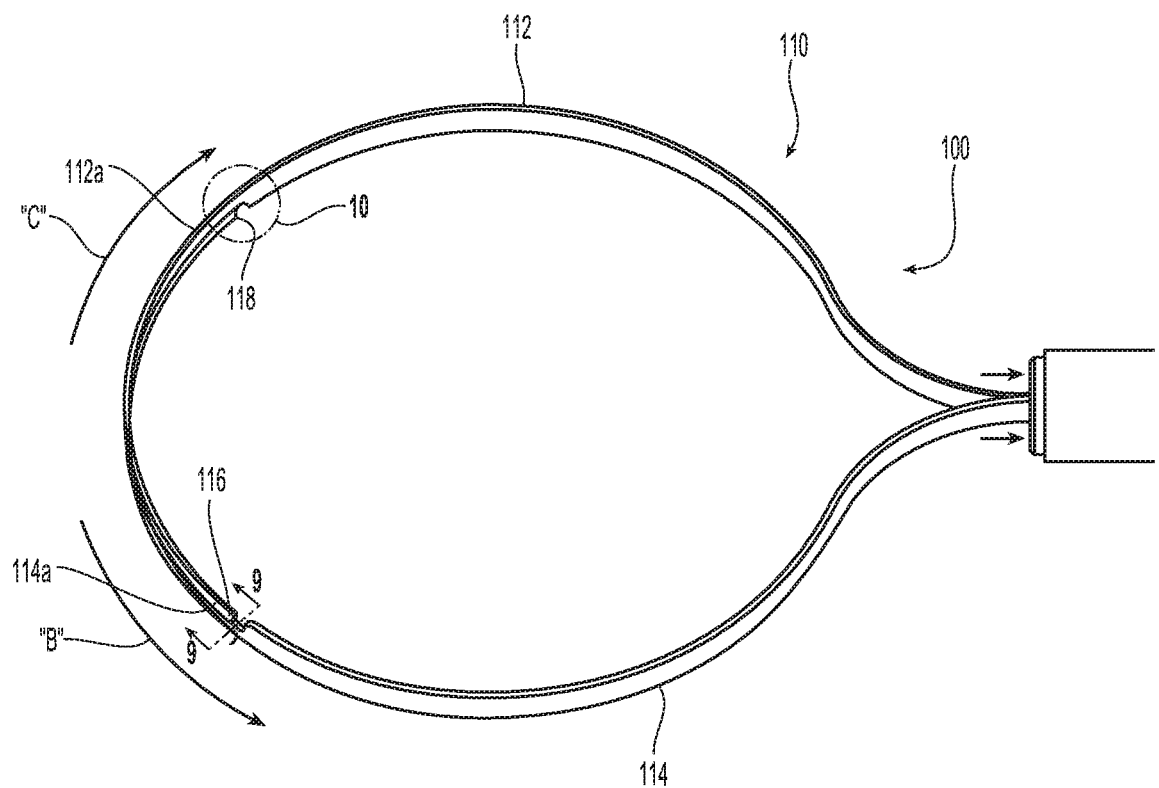
FIG. 8 is a perspective view of a distal portion of another embodiment of a specimen retrieval device in accordance with the principles of this disclosure.
Figure 9:
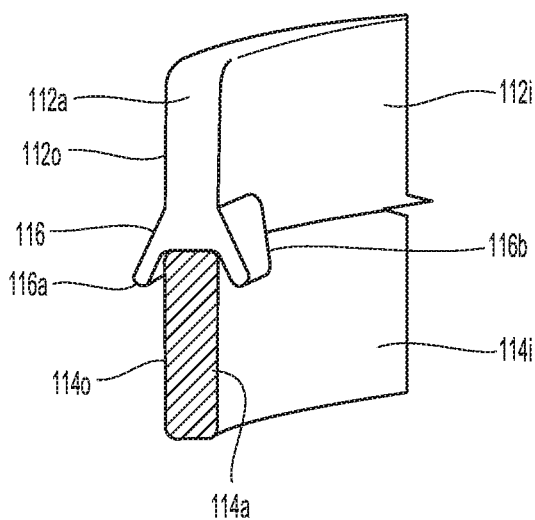
FIG. 9 is an enlarged, cross-sectional view, of the specimen retrieval device of FIG. 8 as taken along section line 9-9 shown in FIG. 8.
Figure 10:
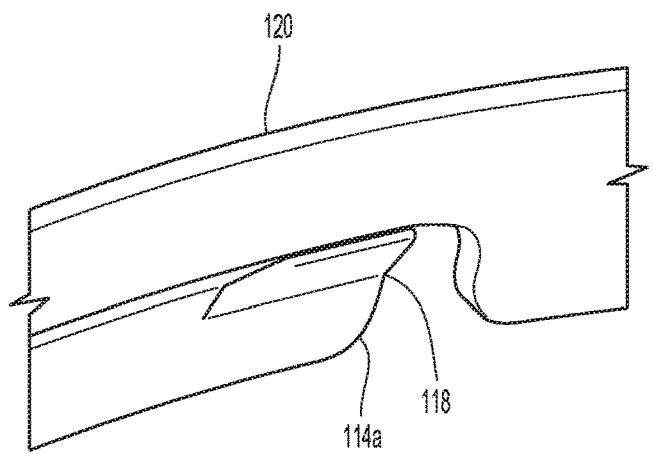

FIGS. 8-10 illustrate another embodiment of a specimen retrieval apparatus 100 that is similar to specimen retrieval apparatus 10, but includes an end effector 110 having a first arm 112 and a second arm 114. First arm 112 extends to a first distal finger 112a and second arm 114 extends to a second distal finger 114a that is configured to be disposed in vertical registration with first distal finger 112a. A distal end portion of first distal finger 112a includes a first winged detent 116 having an outer wing 116a and an inner wing 116b. Outer wing 116a is configured to extend downwardly over an outer surface 114o of second distal finger 114a and inner wing 116b is configured to extend downwardly over an inner surface 114i of distal finger 114a. Similarly, a distal end portion of second distal finger 114a includes a second winged detent 118 with inner and outer wings 120 that are configured to extend upwardly over inner and outer surfaces 112i, 112o of first distal finger 112a so as to mirror first winged detent 116 of first distal finger 112a. First and second winged detents 116, 118 may have U-shaped configurations as seen in FIG. 9. First and second winged detents 116, 118 may be formed by any suitable technique such as stamping. Advantageously, first and second winged detents 116, 118 increase rigidity of end effector 110 and maintain a "slide-to-release" function for bag deployment.

In use, when first and second arms 112, 114 are moved in radially opposite directions, as indicated by arrows "B" and "C," first and second winged detents 116, 118 (e.g., camming/contacting surfaces thereof) slid or cam over first and second distal fingers 112a, 114a, respectively, to separate first and second arms 112, 114 for selectively releasing a collection bag, such as collection 70 (FIG. 1) that is supported on end effector 110 of specimen retrieval device 100.

In some embodiments, first and/or second winged detents 116, 118 may include fewer or more wings. In one embodiment, first and/or second winged detents 116, 118 include only a single wing. In certain embodiments, the single wing of one of the winged detents 116, 118 is disposed on an inner surface of end effector 100 and the single wing of the other winged detent is disposed on an outer surface of end effector 100. In embodiments, the single wings are disposed on just the inner surface of end effector 100, or, in certain embodiments, just the outer surface of end effector 100.

Figure 11:
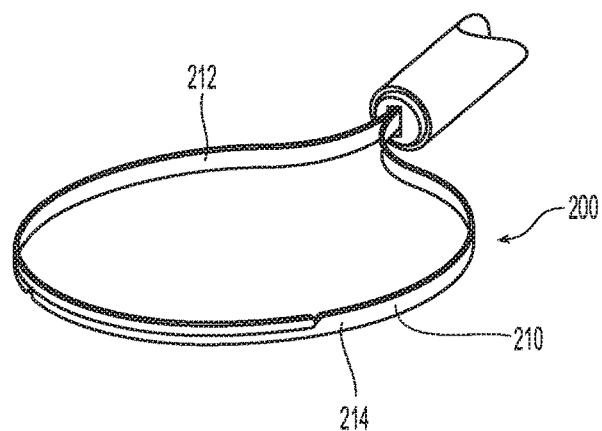
FIG. 11 is a perspective view of a distal end portion of another embodiment of a specimen retrieval device in accordance with the principles of the disclosure.
Figure 12:
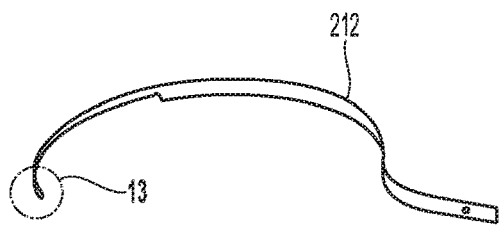
FIG. 12 is a perspective of an arm of the specimen retrieval device of FIG. 11.
Figure 13:
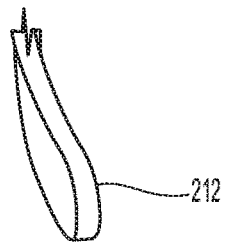
FIG. 13 is an enlarged view of the indicated area of detail shown in FIG. 12.

FIGS. 11-13 illustrate another embodiment of a specimen retrieval apparatus 200 that is similar to specimen retrieval apparatus 100, but includes an end effector 210 having first and second arms 212, 214 without any detents.

In some embodiments, the arms of the disclosed end effectors may be formed of any suitable material, which may be shape memory material such as nitinol.

Securement of any of the components of the disclosed devices may be effectuated using known securement techniques such welding, crimping, gluing, heat-shrinking, fastening, etc.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Pat. No. 8,828,023, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that this disclosure is not limited to the precise embodiments described, and that various other changes and modifications may be effected by one skilled in the art without departing from the scope or spirit of this disclosure. Additionally, the elements and features shown or described in connection with certain embodiments may be combined with the elements and features of certain other embodiments without departing from the scope of this disclosure, and that such modifications and variations are also included within the scope of this disclosure. Accordingly, the subject matter of this disclosure is not limited by what has been particularly shown and described.

The invention claimed is:

1. A specimen retrieval device, comprising:
    an elongated shaft assembly having a proximal end portion and a distal end portion;
    an end effector supported on the distal end portion of the elongated shaft assembly and including a first arm and a second arm, the first arm including a first distal finger, the second arm including a second distal finger, the first and second distal fingers configured to selectively engage one another to support a collection bag on the first and second arms, wherein the first and second distal fingers are secured together with a suture to prevent the first and second distal fingers from moving relative to one another.

2. The specimen retrieval device of claim 1, wherein the first distal finger defines an opening therethrough and the second distal finger defines an opening therethrough, the openings of the first and second distal fingers configured to receive the suture therethrough.

3. The specimen retrieval device of claim 1, further comprising a stationary handle and a movable handle supported on the proximal end portion of the elongated shaft assembly, the movable handle movable relative to the stationary handle to move the end effector between a closed position and an open position.

4. The specimen retrieval device of claim 3, further comprising the collection bag, the first and second arms configured to retain the collection bag on the end effector when the end effector is in the closed position, the first and second arms configured to release the collection bag from the end effector when the end effector is in the open position.

5. A specimen retrieval system, comprising:
a collection bag;
a first arm having a first distal finger supported on a distal end portion of the first arm; and
a second arm having a second distal finger supported on a distal end portion of the second arm, the first and second arms selectively movable relative to one another to releasably secure the collection bag on the first and second arms, the first and second distal fingers disposed in slidable engagement to retain the collection bag on the first and second arms, wherein the first and second distal fingers are secured together with a suture to prevent the first and second distal fingers from moving relative to one another.

6. The specimen retrieval system of claim 5, wherein the first distal finger defines an opening therethrough and the second distal finger defines an opening therethrough, the openings of the first and second distal fingers configured to receive the suture therethrough.

7. A specimen retrieval device, comprising:
an outer shaft having a stationary handle on a proximal end portion thereof;
an inner shaft supported within the outer shaft and having a movable handle on a proximal end portion thereof, the movable handle positioned to move relative to the stationary handle;
a first arm having a proximal end portion secured to the inner shaft and distal end portion having a first distal finger;
a second arm having a proximal end portion secured to the inner shaft and distal end portion having a second distal finger, the first and second distal fingers configured to move in opposite directions as the movable handle moves relative to the stationary handle, wherein the first and second distal fingers are secured together with a suture to prevent the first and second distal fingers from moving relative to one another.

* * * * *